United States Patent
Wohland et al.

(10) Patent No.: US 6,813,569 B2
(45) Date of Patent: Nov. 2, 2004

(54) ASSEMBLY AND METHOD FOR A CORRELATOR STRUCTURE

(75) Inventors: Thorsten Wohland, Singapore (SG); Horst Vogel, Préverenges (CH); Rudolf H. A. Rigler, Danderyd (SE)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 179 days.

(21) Appl. No.: 10/257,281
(22) PCT Filed: Apr. 12, 2001
(86) PCT No.: PCT/CH01/00239
§ 371 (c)(1), (2), (4) Date: Nov. 4, 2002
(87) PCT Pub. No.: WO01/79820
PCT Pub. Date: Oct. 25, 2001

(65) Prior Publication Data
US 2004/0034503 A1 Feb. 19, 2004

(30) Foreign Application Priority Data
Apr. 13, 2000 (CH) .......................... CH00/00217

(51) Int. Cl.[7] .............................. G06F 19/00
(52) U.S. Cl. .................. 702/40; 709/189; 709/179; 600/453
(58) Field of Search ............... 702/179, 189, 702/40; 600/453

(56) References Cited

U.S. PATENT DOCUMENTS 6,322,510 B1 * 11/2001 Kataoka et al. ............. 600/453

FOREIGN PATENT DOCUMENTS

EP          0 175 545           3/1986

OTHER PUBLICATIONS

Kask et al, "Statistical Accuracy in Fluorescence Fluctuation Experiments" European Biophysics Journal, Springer, Tokyo, JP, vol. 25, No. 3, 1997, pp. 163–169.

Rigler et al, "Fluorescence Correlation Spectroscopy with High Count Rate and Low Background: Analysis of Translational Diffusion", European Biophysics Journal, Springer, Tokyo, JP, vol. 22, No. 3, Aug. 1, 1993, pp. 169–175.

Rigler, "Fluorescence Correlation Spectroscopy and Application to the Study of Brownian Motion of Biopolymers", Physica Scripta, Stockholm, SE, vol. 19, 1979, pp. 486–490.

* cited by examiner

Primary Examiner—John Barlow
Assistant Examiner—Stephen J. Cherry
(74) Attorney, Agent, or Firm—Nixon & Vanderhye P.C.

(57) ABSTRACT

The invention concerns an assembly comprising: (a) means for determining the intensity of a plurality of electromagnetic signals, (b) a correlator for correlating or autocorrelating said signals, (c) means for continuously calculating the variance and/or the standard deviation of said signals. It also concerns a method for analysing the intensity of a plurality of electromagnetic radiations scattered and/or emitted from solid, fluid or gaseous samples.

2 Claims, 2 Drawing Sheets

ASSEMBLY AND METHOD FOR A CORRELATOR STRUCTURE

This application is the U.S. national phase of international application PCT/CH01/00239 filed Apr. 12, 2001 which designated the U.S.

The present invention relates to an assembly and a method for a correlator structure. More precisely it concerns an assembly and a method for a correlator structure giving direct access to measurement errors such as the variance and the standard deviation.

Correlation and autocorrelation analyses are methods to test for the dependence of signals on each other or on themselves in space or time. Two signals A and B are said to be correlated in space or time if signal A at a certain position or time depends on the value of signal B at a certain distance in space or time from A. That is, if one knows the value of one of the signals A or B one can infer characteristics of the other signal B or A. This analysis is possible not only for different signals and their mutual correlation (cross correlation) but as well for one signal and its correlation with itself (autocorrelation). For instance, if one observes a signal in time, this signal will undergo characteristic fluctuations. These fluctuations will depend on the underlying process or processes that cause these fluctuations. Thus one can gain insight into these processes if one studies the fluctuations. This is typically done by an autocorrelation analysis which will determine the length and number of the fluctuations. A typical example of this is Fluorescence Correlation Spectroscopy (FCS). FCS is an easy to apply optical method which was introduced more than two decades ago (Ehrenberg, M., and Rigler, R. (1974) Chem. Phys. 4, 390–401; Elson, E. L., and Madge, D. (1974) Biopolym. 13, 1–27; Madge, D., Elson, E. L., and Webb, W. W. (1974) Biopolym. 13, 1–27; Ehrenberg, M., and Rigler, R. (1976) Quart. Rev. Biophys. 9, 69–81) and has been reviewed by several authors (Thompson, N. L. (1991) in Topics in fluorescence spectroscopy, Volume 1: Techniques (Lakowicz, J. R., Ed.) pp 337–378, Plenum Press, New York: Rigler, R., Widengren, J., and Mets, Ü. (1992) in Fluorescence Spectroscopy (Wolfbeis, O. S., Ed.) pp 13–24, Springer-Verlag, Berlin/Heidelberg/New York; Widengren, J. (1996) in Department of Medical Biophysics, Karolinska Institute, Stockholm, Sweden; Widengren, J., and Rigler, R. (1998) Cell. Mol. Biol. 44, 857–879).

FCS uses statistical fluctuations in the fluorescence intensity of a small illuminated sample volume, usually a confocal volume element, to obtain information about the processes that provoke these fluctuations. Processes that can be characterized by this method are in general equilibrium fluctuations (e.g. translational and rotational diffusion, reversible chemical reactions, lifetimes of excited states) but can include as well non-equilibrium processes as, for instance; enzymatic reactions (Edman, L., Foldes Papp, Z., Wennmalm, S., and Rigler, R. (1999) Chem. Phys. 247, 11–22). From these measured parameters information can be obtained about processes that influence these parameters, e.g. oligomerization and aggregation influence the diffusion coefficients of the fluorescent particles and can thus be monitored by this method (e.g. (Rauer, B., Neumann, E., Widengren, J., and Rigler, R. (1996) Biophys. Chem. 58, 3–12; Schuler, J., Frank, J., Trier, U., Schafer Korting, M., and Saenger, W. A. (1999) Biochemistry 38, 8402–8408; Wohland, T., Friedrich, K., Hovius, R., and Vogel, H. (1999) Biochem. 38, 8671–8681). Especially in the last years it has been shown that FCS is a very useful tool in biological research (e.g. (Brock, R., Hink, M., and Jovin, T. (1998) Biophys. J. 75, 2547–2557; Brock, R., and Jovin, T. M. (1998) Cell. and Mol. Biol. 44, 847–856; Rigler, R., Pramanik, A., Jonasson, P., Kratz, G., Jansson, O. T., Nygren, P., Stahl, S., Ekberg, K., Johansson, B., Uhlen, S., Uhlen, M., Jornvall, H., and Wahren, J. (1999) Proc. Natl. Acad. Sci. USA 96, 13318–13323; Schwille, P., Haupts, U., Maiti, S., and Webb, W. W. (1999) Biophys. J. 77, 2251–2265; Schwille, P., Korlach, J., and Webb, W. W. (1999) Cytometry 36, 176–182), and that FCS has great potential in industrial applications, especially in high-throughput screening (Rogers, M. V. (1997) Drug Discovery Today 2, 156–160; Sterrer, S., and Henco, K. (1997) J Recept Signal Transduct Res 17, 511–520; Auer, M., Moore, K. J., MeyerAlmes, F. J., Guenther, R., Pope, A. J., and Stoeckli, K. A. (1998) Drug Discovery Today 3, 457–465; Winkler, T., Kettling, U., Koltermann, A., and Eigen, M. (1999) Proc. Natl. Acad. Sci. USA 96, 1375–1378).

One of the remaining problems is the evaluation of the autocorrelation functions (ACF) measured by FCS. To obtain correct parameter estimations the ACFs have to be fitted with a valid mathematical model. But the decision on the validity of this model and on the quality of the fit depends on detailed knowledge of the accuracy of the particular values in the autocorrelation function (Meseth, U., Wohland, T., Rigler, R., and Vogel, H. (1999) Biophys. J. 76, 1619–1631). This information is contained in the variance of the measured ACF. Although the statistical accuracy of FCS measurements was treated theoretically and experimentally by several authors (Meseth, U., Wohland, T., Rigler, R., and Vogel, H. (1999) Biophys. J. 76, 1619–1631; Koppel, D. E. (1974) Phys. Rev,. A 10, 1938–1945; Qian, H. (1990) Biophys. Chem. 38, 49–57; Kask, P., Gunther, R., and Axhausen, P. (1997) Eur. Biophys. J. 25, 163–169)), the variance and standard deviation of the autocorrelation function was neither directly calculated nor measured. Analytical calculations of the variance were done for exponential functions (Koppel, D. E. (1974) Phys. Rev. A 10, 1938–1945) but are of limited value because most measured autocorrelation functions show non-exponential characteristics (non-exponential dependence is a direct result of the excitation intensity profile which is usually not uniform as assumed for instance in the calculations by Koppel mentioned above (Elson, E. L., and Madge, D. (1974) Biopolym 13, 1–27). Analytical calculations for a non-exponential dependence is in general not possible because the calculations involve often non-converging integrals and thus numerical solutions have to be found.

The application of fluctuation measurements for the calculation of correlation functions is known from EP 175545. The manipulation of time series is disclosed in U.S. Pat. No. 4,954,981. Nevertheless, none of those document takes into account the necessity of measuring the variance of an ACF online. EP 175545 describes the general method of measuring correlations in a liquid medium but it takes not account of the necessity to calculate the variance of the measurement for an efficient data evaluation. On the other side, U.S. Pat. No. 4,954,981 describes the manipulation of time series but needs these time series completely present in memory and gives no solution for the online calculation of the variance.

Therefore it is of utmost importance to develop a method that can calculate the variance of an autocorrelation function directly from the measurements without any assumptions or conditions on the experiment. To ensure that the method does not compromise the feasibility of the measurement two additional constraints have to be considered:

1) The measurement time and evaluation time should be kept as short as possible to allow the measurement of large sample numbers. 2) The amount of stored data should be as small as possible, so that it can still be easily and quickly managed.

For instance, it is possible to estimate the variance by repeating a measurement several times (for adequate statistics typically at least 10 times), but this automatically increases the measurement times several fold and thus decreases the number of possible measurements by the same factor thus violating the first constraint. The second constraint is important because the variance could be calculated by storing the complete set of intensity data and then evaluating these intensity traces. But this will lead to very large amounts of data that will be difficult to treat, and whose evaluation will take additional time.

As it will be explained further in the text, for the present invention we use two new methods that calculate the variance and standard deviation online, i.e. during the measurement, directly from the measured intensity values. These methods avoid the storage of large amounts of intensity values and evaluate the variance simultaneously with the ACF thus leading to no increase in the evaluation time. Both methods can be used in hardware as well as in software correlators, independent of the particular correlator stricture (linear correlators, multiple-tau correlators, etc.).

The autocorrelation function $G(\tau)$ of a fluorescence signal $F(t)$ is defined as follows:

$$G(\tau) = \frac{\langle F(t)F(t+\tau)\rangle}{\langle F(t)\rangle^2} = \frac{\langle F(0)F(\tau)\rangle}{\langle F(0)\rangle^2}. \qquad (1)$$

The angular brackets <> indicate a time average, F is the fluorescence signal as a function of time, and $\tau$ is the correlation time. The right hand side of eq. 1 is valid if the processes under investigation are stationary, i.e. if they are invariant to translation in time. This requirement is very important in FCS and is generally fulfilled. In the ideal case $G(\tau)$ is a continous function of $\tau$. But in actual measurements the fluorescence intensity is measured in channels with a finite time length $\Delta\tau$ and thus the experimental ACF is calculated at discrete times. The number of photons countetd in a channel at a certain time $i^*\Delta\tau$, with i being an integer number, are denoted by $n(i^*\Delta\tau)$. The length of $\Delta\tau$, and the time $i^*\Delta\tau$ at which measurements are taken can vary from correlator to correlator or even within a correlator (multiple-tau correlators). With this definition the autocorrelation function can be written as:

$$G_i(m\Delta\tau_i) = \frac{\frac{1}{M-m}\sum_{k=1}^{M-m} n(k\Delta\tau_i)n(k\Delta\tau_i+m\Delta\tau_i)}{\left(\frac{1}{M-m}\sum_{k=1}^{M-m} n(k\Delta\tau_i)\right)\cdot\left(\frac{1}{M-m}\sum_{k=m}^{M} n(k\Delta\tau_i)\right)} \qquad (2)$$

Here, m is an integer number, $\Delta\tau_i$ is the sampling time (channel width) of channel i, and $m\Delta\tau_i$ is the correlation time. M is the number of measurements with length $\Delta\tau_i$, and is given by $M=T/\Delta\tau_i$, where T is the total measurement time. $n(k\Delta\tau_i)$ is the number of photons at time $k\Delta\tau_i$, sampled with a channel width of $\Delta\tau_i$, and $n(k\Delta\tau_i+m\Delta\tau_i)$ the number of photons a time $m\Delta\tau_1$ later. The ACF is symmetrically normalized (Schätzel, K., Drewel, M., and Stimac, S. (1988) *J. Mod. Opt.* 35, 711–718; Schätzel, K. (1991) in *Photon Correlation Spectroscopy Multicompononet system* (Schmitz, K. S., Ed.) pp 109–115).

A similar defintion can be given for the cross-correlation of two signals, where one of the two measurement values $(n(k\Delta\tau_i)$ or $n(k\Delta\tau_i+m\Delta\tau_i))$ in eq. 2 has to be exchanged for another measurement signal $(q(k\Delta\tau_i)$ or $q(k\Delta\tau_i+m\Delta\tau_i)$, e.g. (Schwille, P., Meyer-Almes, F., and Rigler, R. (1997) *Biophys. J.* 72,1878–1886; Kettling, U., Koltermann, A., Schwille, P., and Eigen, M. (1998) *Proc. Natl. Acad. Sci. USA* 95, 1416–1420):

$$G_{nq,i}(m\Delta\tau_i) = \frac{\frac{1}{M-m}\sum_{k=1}^{M-m} n(k\Delta\tau_i)q(k\Delta\tau_i+m\Delta\tau_i)}{\left(\frac{1}{M-m}\sum_{k=1}^{M-m} n(k\Delta\tau_i)\right)\cdot\left(\frac{1}{M-m}\sum_{k=m}^{M} q(k\Delta\tau_i)\right)} \qquad (2a)$$

or $$G_{qn,i}(m\Delta\tau_i) = \frac{\frac{1}{M-m}\sum_{k=1}^{M-m} q(k\Delta\tau_i)n(k\Delta\tau_i+m\Delta\tau_i)}{\left(\frac{1}{M-m}\sum_{k=1}^{M-m} q(k\Delta\tau_i)\right)\cdot\left(\frac{1}{M-m}\sum_{k=m}^{M} n(k\Delta\tau_i)\right)} \qquad (2b)$$

All following explanations will be given for eq. 2 only, but are straightforward to generalize for eqs. 2a and 2b.

Most commercially available hardware correlators calculate the ACF according to eq. 2 online without giving access to the intensity measurements n(t). This is the case since the storage of the intensity data is difficult due to the amount of data. Molecular processes have characteristic time constants $\tau_p$ that vary between typically nanoseconds and milliseconds. To measure such processes, intensity values have to be taken faster than the fastest process to be measured ($\Delta\tau<<\tau_p$, see as well Patent EP 175545) and the duration T of the measurement has to be long enough so that one averages over a large number of single processes ($T>>\tau_p$). Therefore the amount of intensity values typically taken per second are in the order of $10^6$–$10^8$. This amount of data is too large to be stored efficiently. Therefore an effective method is required to calculate the variance directly online parallel to the ACF without the need to store the whole intensity data set.

More recently two new hardware correlators came to the market which actually give access to the intensity data (Correlator.com, Bridgewater, 08807 N.J., USA; (Eid, J. S., Müller, J. D., and Gratton, E. (2000) *Rev. Sci. Instr.* 71, 361–368). But they still require lengthy data treatment procedures afterwards using suitable software to calculate standard deviations or even correlations. Both correlators are not able to calculate the variance or standard deviation online but rely on the storage of the whole intensity data.

With the present invention the variance ($\sigma^2$) and standard deviation ($\sigma$) can be calculated for each point in the ACF directly from the intensity data. This can be done in two ways:

1) By determining the standard error of the mean (sometimes also called "variance of the mean" or "variance of the sample mean", (Davenport, W. B. J., and Root, W. L. (1958) *An Introduction to the Theory of Random Signals and Noise*, McGraw-Hill, New York; Bevington, P. R., and Robinson, D. K. (1992) *Data reduction and error analysis for the physical sciences*, 2. ed., McGraw Hill, New York) of eq. (2). Every point calculated in the ACF is a normalized average value. The standard error of the mean is defined as $$\sigma_{SEM}(x) = \frac{\sqrt{\langle x^2\rangle - \langle x\rangle^2}}{\sqrt{N}} \qquad (3)$$

and calculates the error of the average value <x>. x is the variable for which the average is calculated, and N is the number of measurement points taken. In our case $x=n(k\Delta\tau_i)$ $n(k\Delta\tau_i+m\Delta\tau_i)$ and N corresponds to the value of M−m defined above (eq. (2)). Thus the standard deviation of the mean for the ACF is calculated by $$\sigma_{SEM}(G(m\Delta\tau_i)) = \frac{\left[\frac{1}{M-m}\left(\sum_{k=1}^{M-m} n^2(k\Delta\tau_i)n^2(k\Delta\tau_i+m\Delta\tau_i)\right) - \frac{1}{(M-m)^2}\left(\sum_{k=1}^{M-m} n(k\Delta\tau_i)n(k\Delta\tau_i+m\Delta\tau_i)\right)^2\right]^{1/2}}{\sqrt{M-m}\cdot\left(\frac{1}{M-m}\sum_{k=1}^{M-m} n(k\Delta\tau_i)\right)\cdot\left(\frac{1}{M-m}\sum_{k=m}^{M} n(k\Delta\tau_i)\right)}. \quad (4)$$

This value can be determined for every point in the ACF and gives an estimate of the variance and standard deviation of every individual point.

2) By dividing the measurement time in N subsets, and calculating parallel to the ACF as well the autocorrelation functions $G_h(\tau)$ for every subset h ($1\leq h\leq N$). Using again the definition of the standard error of the mean, the variance and standard deviation can be calculated by comparing the N ACFs (denoted $G_h(\tau)$) calculated for the N time intervals (subsets). From the $G_h(\tau)$ the standard deviation of the ACF can then be calculated in the following way:

$$\sigma_{SEM}(G_i(m\Delta\tau)) = \frac{\sqrt{\frac{1}{N}\sum_{h=1}^{N} G_{i,h}^2(m\Delta\tau_i) - \left(\frac{1}{N}\sum_{h=1}^{N} G_{i,h}(m\Delta\tau_i)\right)^2}}{\sqrt{N}}. \quad (5)$$

Both methods rely on the calculation of the standard error of the mean of a variable. While in method 1) the standard error of the mean is calculated over all products $n(k\Delta\tau_i)*n(k\Delta\tau_i+m\Delta\tau_i)$, in method 2) the standard error of the mean is calculated for N correlation functions $G_h(\tau)$ which were determined on N different time intervals of length T/N, where T is the total measurement time. Both methods give an estimation of the variance and standard deviation of the ACF determined over the whole measurement time T. While method 1) needs less values to be stored (see next paragraph), method 2) delivers slightly better estimations for the variance of the measurement as we were able to show by simulations (unpublished data).

It is important to note here that both methods calculate the variance and standard deviation online and avoid the storage of the whole intensity data set, thus fulfilling the constraints defined in the introduction, namely no increase in measuring time and avoidance of the storage of large amounts of data.

Taking into account above equations (4) or (5) present invention more precisely relates to an assembly comprising:

a) means for determining the intensity of a plurality of electromagnetic radiation scattered and/or emitted from solid, fluid or gaseous samples. The intensity may be recorded by e.g. photomultipliers, avalanche photodiodes, charge coupled devices or other type of detectors b) means for storing the recorded intensity traces continuously or batch wise in single and/or multiple form (e.g. at different scattering angles, different wavelengths, different temperatures and other sample conditions), c) means for calculating correlation functions of different orders e.g.: self-correlation function, second and higher order correlation functions including cross-correlation functions. Calculation can be performed from traces obtained continuously and/or batch wise and optionally including the multiple tau format, d) means for calculating in continuous and/or batch wise mode, optionally including the multiple tau format, the variance and/or standard deviations from the stored signal traces according to above cited equations (4) or (5)

e) hardware and/or software devices which represent traces, correlation functions and variance/standard deviation plots simultaneously Present invention also concern a method for analysing the intensity of a plurality of electromagnetic radiations scattered and/or emitted from solid fluid or gaseous samples comprising the following steps:

a) determining the intensity of said electromagnetic radiations, b) storing the recorded intensity traces continuously and/or batch wise in single and/or multiple form, c) calculating correlation functions of different orders from intensity traces obtained continuously and/or batch wise, d) calculating continuously the variance and/or standard deviations from the stored signal traces according to above equations (4) or (5).

e) displaying simultaneously said intensity traces, correlation functions and variance/standard deviation plots on a hardware and/or a software device.

The invention will be exemplified hereafter in using following figures.

Figure 1:
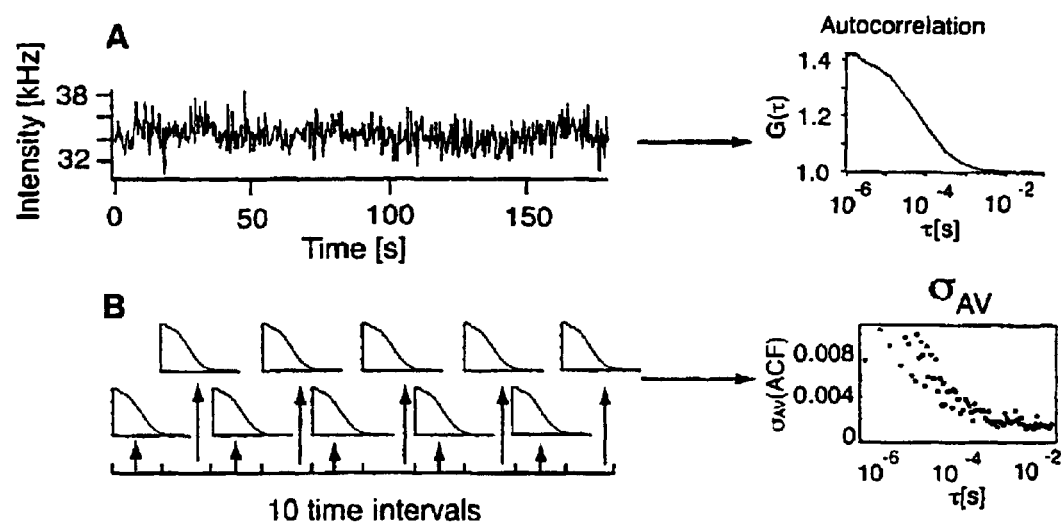
FIG. 1 illustrates the calculation of standard deviation according to above eq. (5)

Referring to FIG. 1, in part A the intensity trace recorded over 180 s is correlated and leads to the depicted ACF. In part B the intensity trace from A is divided in 10 subsets of equal length (18 s) and each subset leads to one ACF. For these 10 ACFs the standard deviation can be calculated ($\sigma_{AV}$), as is shown in the right part of the picture. $\sigma_{AV}$ is now valid for the ACFs which were calculated for the traces of 18 s. To arrive at standard deviation which is valid for the ACF which is calculated for the 180 s intensity trace it has to be divided by the square root of the number of subsets (see eq. 3): $\sigma_{AV}/\sqrt{10}$.

Standard correlators calculate the following values for every point in the ACF online and store them (see eq. 2):

$$\frac{1}{M-m}\sum_{k=1}^{M-m} n(k\Delta\tau_i)n(k\Delta\tau_i+m\Delta\tau_i) \quad (6a)$$

$$\frac{1}{M-m}\sum_{k=1}^{M-m} n(k\Delta\tau_i) \quad (6b)$$

$$\frac{1}{M-m}\sum_{k=m}^{M} n(k\Delta\tau_i) \quad (6c)$$

If the ACF contains P number of points, at most 3*P values have to be stored (P is usually in the range of 100–500). Compared with the number of intensity values measured ($10^6$–$10^8$) this is at least a factor of $10^3$–$10^4$ less data to be stored.

With method according to above eq. (4) only the following value has to be stored additionally for every point in the ACF:

$$\frac{1}{M-m}\left(\sum_{k=1}^{M-m} n^2(k\Delta\tau_i)n^2(k\Delta\tau_i + m\Delta\tau_i)\right) \quad (6d)$$

This increases the amount of data by only a third to 4*P values and allows now an efficient calculation of the variance and standard deviation of the ACF.

For method according to above eq. (5) more data points have to be stored. To calculate the N ACFs for the N subsets one has to calculate the 3*P values for every subset, resulting in 3*N*P values to be stored (in general N is at least 10). From these values the ACF (eq. 2) for the total measurement time and its standard deviation (eq. 5) can be directly calculated.

We performed simulations and experiments to show that the two methods presented above efficiently describe the standard deviation and significantly improve present estimations schemes based on Koppel's formula (Koppel, D. E. (1974) *Phys. Rev. A* 10, 1938–1945)).

Fluorescence data were acquired with a data acquisition bord (PCI-MIO-16-E-1 National Instruments, Geneva, Switzerland), and then correlated by software written in the programming language C on a UNIX system.

Simulations were performed by simulating 69 particles in a sphere of 3 μm radius (corresponding to about 1 nM concentration) with a time step $\Delta_1$ of 0.2 μs. The jump distance σ of the particles was calculated according to the equation of diffusion (Chandrasekhar, S. (1943) *Rev. Mod. Phys.* 15, 1–89) for the corresponding diffusion coefficient (e.g., 18 nM jump distance corresponds to a diffusion coefficient of D=2.7 $10^{-6}$ cm$^2$/s).

$$\sigma = \sqrt{6D\Delta_t} \quad (7).$$

All calculations were done assuming a multiple-tau correlator (Schätzel, K., Drewel, M., and Stimac, S. (1988) *J. Mod. Opt.* 35, 711–718; Schätzel, K. (1991) in *Photon Correlation Spectroscopy Multicomponent system* (Schmitz, K. S., Ed.) pp 109–115). (Schätzel, K. (1985) *Inst. Phys. Conf. Ser.* 77, 175–184; Schätzel, K. (1987) *Appl. Phys. B* 42, 193–213; ALV-Vertriebsgesellschaft (1993) *ALV-5000-Manual, Multiple Tau Digital Correlator-Reference*, Langen, Germany). In this correlator structure, the ACF is calculated with channels whose length Δτ varies with the correlation time. For longer correlation times longer channels are used and the number of calculations is also significantly reduced. Thus one works with channel lengths in the microsecond range for correlation times in the same range but one works with channel lengths of milliseconds when one calculates the ACF in the millisecond time range. Thus the number of calculations stays nearly constant in every decade of correlation time that is calculated.

Figure 2:
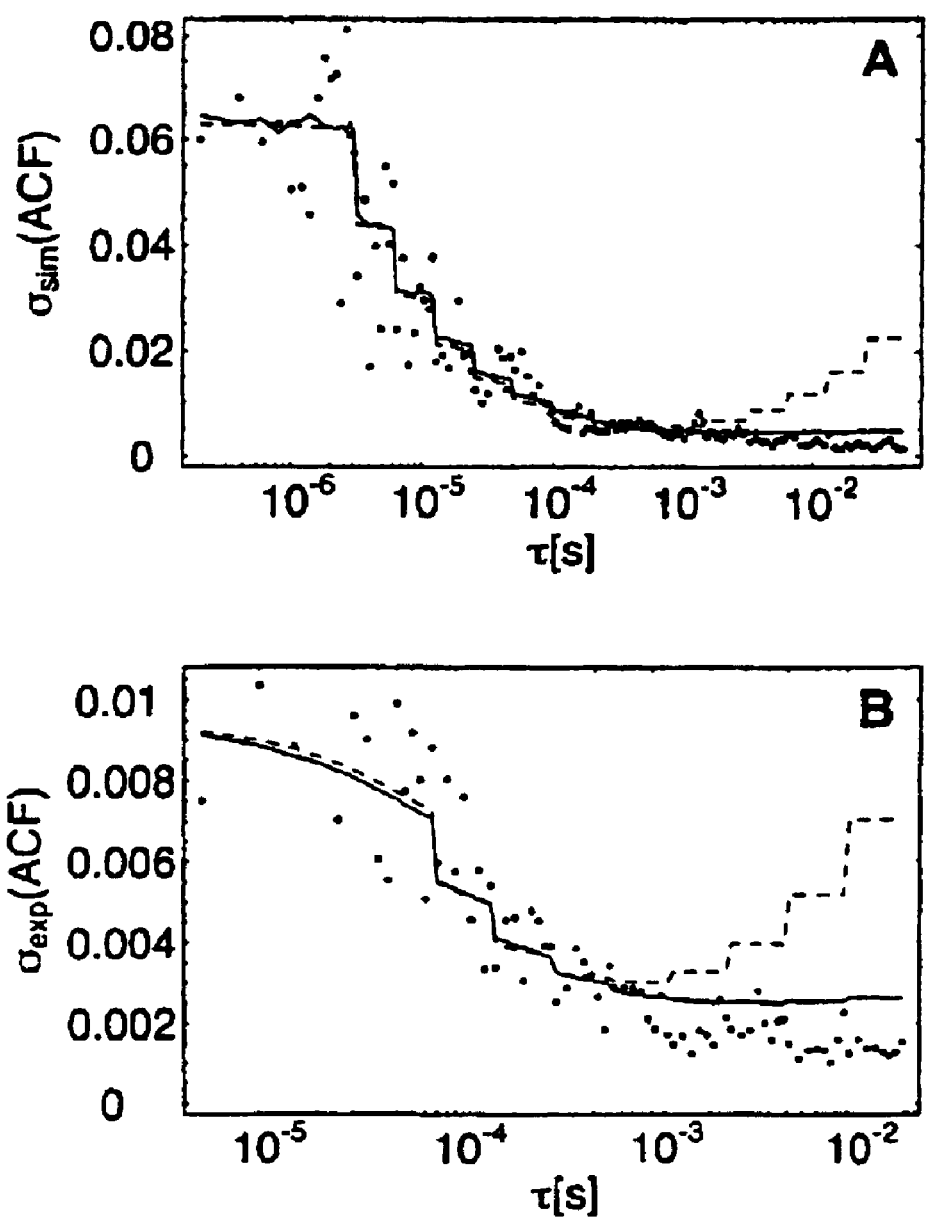
FIG. 2 illustrates standard deviations of simulated and experimental autocorrelation functions.

Referring to FIG. 2 we can see Standard Deviation $\sigma_{sim}$(ACF) and $\sigma_{exp}$(ACF) of the simulated (see part A) and experimental (see part B)autocorrelation functions. The points are the standard deviation calculated by averaging 10 ACFs. While this procedure is not practical because it needs 10 times longer measurement times, it is a good standard with which other methods can be compared. The dashed lines are the standard deviation calculated by Koppel's formula. They clearly deviate from the real standard deviation represented by the points. The solid line represents the standard deviation calculated by method according to eq. 4.

It is clear that this method clearly performs better than Koppel's formula and approximates the real standard deviation to a high degree. Similar graphs can be shown as well for method according to eq. 5.

EXAMPLE 1

In hight-throughput screening (HTS) or ultra hight-throughput screening (uHTS) applications it is extremely important to shorten measurement times as much as possible to maximize the number of samples measurable per day while at the same time it has to be ensured that the data evaluation can extract the information from the measurements with the smallest uncertainties possible. By the methods delineated in this work the measurement time is not affected because the variance and standard deviation are calculated online in parellel with the ACF. At the same time the calculation of the variance allows to efficiently evaluate the data by the possibility to weigh the data points according to their error. Thus points with higher errors (variance) will have less influence on the evaluation than points with lower errors (see data weighting, (Beechem, J. M. (1992) in *Numerical Computer Methods* (Brand, L., and Johnson, M. L., Eds.) pp 37–54, Academic Press, Inc; Johnson, M. L., and Faunt, L. M. (1992) in *Numerical Computer Methods* (Brand, L., and Johnson, M. L., Eds.) pp 1–37, Academic Press, Inc; Di Cera, E. (1992) in *Numerical Computer Methods* (Brand, L., and Johnson, M. L., Eds.) pp 68–87, Academic Press, Inc).

EXAMPLE 2

For the measurement of particle sizes and particle size distributions it is necessary to have a good estimation of the measurement error. The measured correlation data have to be fitted with models featuring a certain number of parameters. The difference between different models in this data fitting procedures can only be made when sufficient knowledge about the measured data is available, including the variance of the measurement (for particle size measurements see: (Starchev, K., Zhang, J., and Buffle, J. (1998) *J. Colloid Interface Sci.* 203, 189–196; Starchev, K., Buffle, J., and Perez, E. (1999) *J. Colloid Interface Sci.* 213, 479–487).

EXAMPLE 3

In a recent paper we have shown that in Fluorescence Correlation Spectroscopy it is possible to determine whether one or two particle species are present in a sample only if their diffusion coefficients differ by a certain factor, depending on the photophysical characteristics of the fluorophores used. Using the calculation of the variance taken for the present invention, these factors could be lowered and it should be possible to determine already for smaller differences in the diffusion coefficient whether one particle species or two are present and thus increasing the time resolution of FCS.

The apparatus and methods of the present invention fulfill both goals. By the development of hardware or software correlators on the basis of the methods according to eq. (4) or (5) one can calculate the variance online by calculating only some additional values during the whole measurement. Therefore it is not necessary to store the whole intensity data (saving time and storage memory), saving in addition the time and work that would be needed to extract the variance from this data offline.

The methods of the present invention allow to calculate the variance numerically directly during measurements from the collected data without loss of measurement speed and without the need to drastically increase storage place. We thus circumvent the problems of analytical solutions: a) diverging integrals which do not allow the calculation of the variance, and b) the incapability to account for systematic and instrumental errors, which are present in the collected data but can not be predicted by analytic solutions.

With the present invention we offer the possibility to calculate directly from the measured data, i.e. the intensity values or photon counts, the variance and standard deviation for correlation functions online, and thus improve data evaluation significantly. Correlation analyses are much faster due to the online calculation of the standard deviation. In addition they allow accurate data treatment which was not possible until now due to the lack of methods to calculate the standard deviation.

What is claimed is:

1. An assembly comprising:
   a) means for determining the intensity of a plurality of electromagnetic radiations scattered and/or emitted from solid fluid or gaseous samples,
   b) means for storing the recorded intensity traces continuously and/or batch wise in single and/or multiple form,
   c) means for calculating correlation functions of different orders from intensity traces obtained continuously and/or batch wise,
   d) means for calculating continuously the variance and/or standard deviations from the stored signal traces according to equation $$\sigma_{SEM}(G(m\Delta\tau_i)) = \frac{\left[\frac{1}{M-m}\left(\sum_{k=1}^{M-m} n^2(k\Delta\tau_i)n^2(k\Delta\tau_i + m\Delta\tau_i)\right) - \frac{1}{(M-m)^2}\left(\sum_{k=1}^{M-m} n(k\Delta\tau_i)n(k\Delta\tau_i + m\Delta\tau_i)\right)^2\right]^{1/2}}{\sqrt{M-m} \cdot \left(\frac{1}{M-m}\sum_{k=1}^{M-m} n(k\Delta\tau_i)\right) \cdot \left(\frac{1}{M-m}\sum_{k=m}^{M} n(k\Delta\tau_i)\right)}$$

or to equation $$\sigma_{SEM}(G_i(m\Delta\tau)) = \frac{\sqrt{\frac{1}{N}\sum_{h=1}^{N} G_{i,h}^2(m\Delta\tau_i) - \left(\frac{1}{N}\sum_{h=1}^{N} G_{i,h}(m\Delta\tau_i)\right)^2}}{\sqrt{N}}$$

e) hardware and/or software devices which represent traces, correlation functions and variance/standard deviation plots simultaneously,
wherein:
   $\sigma_{sem}(G(m\Delta\tau_i))$ is the standard deviation of the mean for the autocorrelation function,
   G is the autocorrelation,
   m is an integer number,
   $\Delta\tau_i$ is the sampling time (channel width) of channel i,
   $m\Delta\tau_i$ is the correlation time, M is the number of measurements with length $\Delta\tau_i$,
$n(k\Delta\tau_i)$ is the number of photons at time $k\Delta\tau_1$, sampled with a channel width of $\Delta\tau_1$,
$n(k\Delta\tau_i+m\Delta\tau_i)$ is the number of photons a time $m\Delta\tau_1$ later, and
N is the number of subsets.

2. Method for analysing the intensity of a plurality of electromagnetic radiations scattered and/or emitted from solid, fluid or gaseous samples comprising the following steps:
   a) determining the intensity of said electromagnetic radiations,
   b) storing the recorded intensity traces continuously and/or batch wise in single and/or multiple form,
   c) calculating correlation functions of different orders from intensity traces obtained continuously and/or batch wise,
   d) calculating continuously the variance and/or standard deviations from the stored signal traces according to equation $$\sigma_{SEM}(G(m\Delta\tau_i)) = \frac{\left[\frac{1}{M-m}\left(\sum_{k=1}^{M-m} n^2(k\Delta\tau_i)n^2(k\Delta\tau_i + m\Delta\tau_i)\right) - \frac{1}{(M-m)^2}\left(\sum_{k=1}^{M-m} n(k\Delta\tau_i)n(k\Delta\tau_i + m\Delta\tau_i)\right)^2\right]^{1/2}}{\sqrt{M-m} \cdot \left(\frac{1}{M-m}\sum_{k=1}^{M-m} n(k\Delta\tau_i)\right) \cdot \left(\frac{1}{M-m}\sum_{k=m}^{M} n(k\Delta\tau_i)\right)}$$

or to equation $$\sigma_{SEM}(G_i(m\Delta\tau)) = \frac{\sqrt{\frac{1}{N}\sum_{h=1}^{N} G_{i,h}^2(m\Delta\tau_i) - \left(\frac{1}{N}\sum_{h=1}^{N} G_{i,h}(m\Delta\tau_i)\right)^2}}{\sqrt{N}}$$

e) displaying simultaneously said intensity traces, correlation functions and variance and/or standard deviation plots on a hardware and/or a software device.
wherein
   $\sigma_{sem}(G(m\Delta\tau_i))$ is the standard deviation of the mean for the autocorrelation function,
   G is the autocorrelation,
   m is an integer number,
   $\Delta\tau_i$ is the sampling time (channel width) of channel i,
   $m\Delta\tau_i$ is the correlation time,
   M is the number of measurements with length $\Delta\tau_i$,
   $n(k\Delta\tau_i)$ is the number of photons at time $k\Delta\tau_1$ sampled with a channel width of $\Delta\tau_1$,
   $n(k\Delta\tau_i+m\Delta\tau_i)$ is the number of photons a time $m\Delta\tau_1$ later, and
   N is the number of subsets.

* * * * *